United States Patent [19]
Hitchcock et al.

[11] Patent Number: 6,069,238
[45] Date of Patent: May 30, 2000

[54] SPIROCYCLIC C-GLYCOSIDES

[75] Inventors: Stephen Andrew Hitchcock; Chafiq Hamdouchi, both of Carmel; Concepcion Sanchez-Martinez, Indianapolis; Almudena Rubio Esteban, Carmel, all of Ind.

[73] Assignee: Eli Lilly and Company, Indianapolis, Ind.

[21] Appl. No.: 09/342,073

[22] Filed: Jun. 28, 1999

Related U.S. Application Data

[60] Provisional application No. 60/102,400, Sep. 30, 1998.
[51] Int. Cl.[7] .............................. C07H 1/00; C07H 15/00; C07H 17/00
[52] U.S. Cl. .................... 536/17.5; 536/17.2; 536/18.1; 536/18.5; 536/18.7; 536/122; 536/124
[58] Field of Search .............................. 536/17.2, 18.1, 536/18.5, 18.7, 122, 124, 17.5

[56] References Cited

PUBLICATIONS

J. Org. Chem., Barrett, A.G.M., (1996), vol. 61, pp. 1082–1100.

*Primary Examiner*—Elli Peselev
*Attorney, Agent, or Firm*—Arlene K. Musser

[57] ABSTRACT

An improved and a new synthetic route for the reparation of spirocyclic C-glycoside compounds having the following general structure are described.

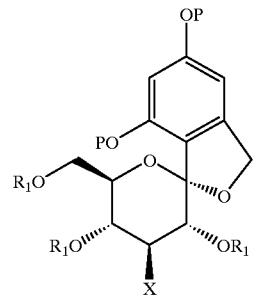

Novel derivatives of spirocyclic C-glycoside compounds are also disclosed which may be used as intermediates in the synthesis and evaluation of potential pharmaceutically active materials.

7 Claims, No Drawings

SPIROCYCLIC C-GLYCOSIDES

CROSS-REFERENCE

This invention claims priority of U.S. Provisional Application Ser. No. 60/102,400, filed Sep. 30, 1998.

FIELD OF THE INVENTION

The present invention relates to processes for the preparation of spirocyclic C-glycosides and novel derivatives thereof.

BACKGROUND

Spirocyclic C-glycosides represent a key structural component of papulacandin compounds and related analogs. Papulacandins are secondary metabolites obtained by the cultivation of a specific strain of *Papularia sphaerosperma* (NRRL 8086) and consist of two primary components A and B in addition to three subsidiary components C, D and E. The papulacandin natural products and related analogs have received attention over the past couple of decades because of their antifungal activity (see e.g., U.S. Pat. Nos. 4,278,665 and 5,091,413; and Traxler, P., et al., "Papulacandins, A New Family of Antibiotics with Antifungal Activity/Structures of Papulacandins A, B, C and D" *J. Antibiotics*, XXXIII(9), 967–978 (1980).) and antipneumocystis activity (see e.g., U.S. Pat. No. 5,089,478). Other compounds related to the papulacandin family where the spiro ring has opened are also known, i.e., chaetiachandin (see Komori, T., et al., "Chaetiacandin, A Novel Papulacandin II. Structure Determination" *J. Antibiotics*, XXXVIII(4), 544–546 (1995).) and fusacandins. The fusacandins have been reported as having antifungal activity (see e.g., U.S. Pat. Nos. 5,773,421 and 5,585,251; and Hochlowski, J. E., et al. "Fusacandins A and B; Novel Antifungal Antibiotics of the Papulacandin Class from Fusarium sambucinum II. Isolation and Structural Elucidation," *J. of Antibiotics*, 48(7), 614–618 (1995).)

Current studies of papulacandin compounds and their analogs have resulted primarily from isolation and modification of the natural products; therefore, derivatization of the compounds is limited. Consequently, there is a need for an efficient means for making key intermediates which provide more flexibility in evaluating potential pharmaceutically active materials that either contain or are derived from spirocyclic C-glycosides.

SUMMARY OF THE INVENTION

The present invention provides improved processes for the preparation of spirocyclic C-glycoside compounds (I) and novel derivatives thereof.

I

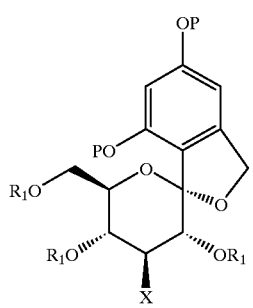

wherein P is H, alkyl (e.g., methyl, ethyl, propyl, butyl, etc.), alkenyl (e.g., vinyl, allyl, etc.), acyl (e.g., acetyl), or a protecting group; X is $OR_1$, $SR_1$, $N_3$ or $NH_n(R_1)_{2-n}$, where $n=0$ or 1; and $R_1$ is the same as P or a sugar moiety.

In one embodiment of the present invention, a process is provided for the preparation of a spirocyclic C-glycoside compound represented by general structure IA

IA

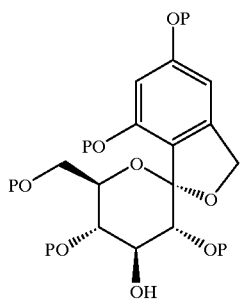

comprising the steps of (i) mixing an alkyl lithium (e.g., methyl lithium, n-butyl lithium, t-butyl lithium, etc.) to a solution of Compound 1(b)

1(b)

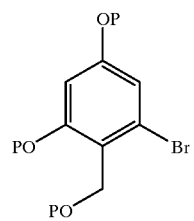

where P is a protecting group, in diethyl ether at −78° C. to form a lithium anion solution; (ii) mixing the lithium anion solution at −78° C. with a solution of Compound 1(a)

1(a)

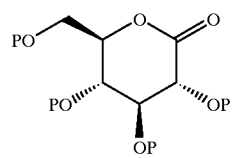

where P is a protecting group, in diethyl ether cooled to −78° C.; (iii) allowing the mixture of step (ii) to warm quickly to room temperature (about 1 hour); and (iv) isolating the desired spirocyclic C-glycoside compound.

In another embodiment of the present invention, a process is provided for the preparation of a spirocyclic C-glycoside compound represented by general structure IB

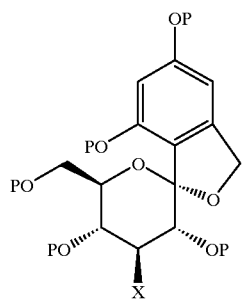

wherein X is OP, SP, or an azide group and P is each independently a hydrogen, alkyl, alkenyl, acyl, or a protecting group, comprising the steps of: (i) condensing iodo Compound 1(a)

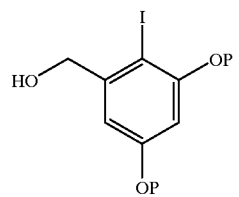

(P has the same meaning as above) with Compound 1(b)

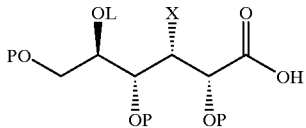

(where P has the same meaning as above and L is a leaving group) to form an ester 1(c)

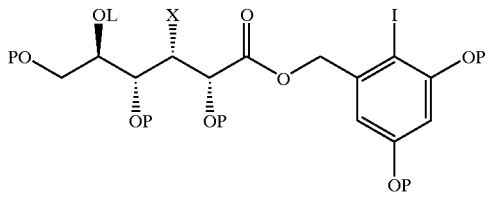

(where P and L have the same meaning as above); (ii) treating said ester 1(c) with an alkyl lithium; and (iii) optionally replacing any P groups that may have been removed during step (ii) with another P group which may be the same or different to form said spirocyclic C-glycoside compound represented by structure I.

The term "leaving group" refers to a group that is capable of being removed from the attached oxygen to form an oxygen anion or hydroxyl group (depending upon the conditions for the removal of the leaving group). Suitable leaving groups include any leaving group known to those skilled in the art, such as those described in described in T. W. Greene, "Protective Groups in Organic Synthesis," John Wiley and Sons, New York, N.Y., (2nd ed., 1991). A preferred leaving group is and acetyl group.

In yet another embodiment of the present invention, the iodo substituent is introduced onto the aromatic ring after condensation between the benzyl alcohol and Compound 1(b) above.

The spirocyclic C-glycoside compounds produced by the processes described herein may be used as intermediates for the preparation of papulacandin compounds and analogs thereof. The improved process provides higher yields than previously reported in the literature. The new synthetic scheme has fewer steps as well as better yields than alternative routes currently described in the literature. In addition, the novel synthetic scheme allows for inclusion of new functionality and protecting groups into both the aryl and carbohydrate portions of the molecule that would be more difficult using existing reported methods.

DETAILED DESCRIPTION

The processes described herein provide an improved procedure and a new synthetic route for the preparation of spirocyclic C-glycoside compounds represented by structure I below.

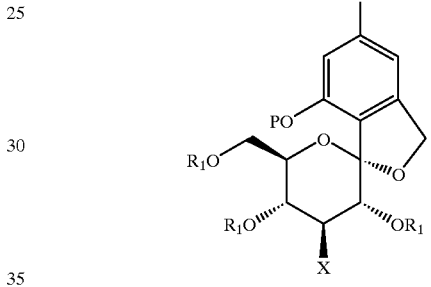

wherein P is H, alkyl (e.g., methyl, ethyl, propyl, butyl, etc.), alkenyl (e.g., vinyl, allyl, etc.), acyl (e.g., acetyl), or a protecting group; X is $OR_1$, $SR_1$, $N_3$, $NH_n(R_1)_{2-n}$, where n=0 or 1; and $R_1$ is the same as defined for P, or a sugar moiety.

As used herein, the term "protecting group" refers to a moiety employed to block or protect the hydroxy, thiol or amino functionality while reactions are carried out on other functional groups on the compound. The substituent when used as a hydroxy protecting group may form an ether (e.g., methyl, methoxymethyl, or benzyloxymethyl ether), a silyl ether (e.g., trimethylsiloxy or t-butyl dimethylsiloxy), an ester (e.g. acetoxy, benzyloxycarbonyl, or t-butoxy carbonyl), or a sulfonate moiety (e.g. methanesulfonate or p-toluenesulfonate). The exact genus and species of hydroxy protecting group is not critical so long as the derivatized hydroxy group is stable to the conditions of subsequent reaction(s) and the protecting group can be removed at the appropriate point without disrupting the remainder of the molecule. A preferred hydroxy protecting group is acetyl. Specific examples of hydroxy and thiol protecting groups are described in T. W. Greene, "Protective Groups in Organic Synthesis," John Wiley and Sons, New York, N.Y., (2nd ed., 1991).

The substituent when used as an amino protecting group may form a cyclic imide, e.g., phthalimido and tetrachlorophthalimido when n is equal to 0. When n is equal to 1, the protecting group can form a carbamate, e.g., methyl, ethyl, and 9-fluorenylmethylcarbamate; or an amide, e.g., N-formyl and N-acetylamide. The exact genus and species of amino protecting group employed is not critical so long as the derivatized amino group is stable to the condition of subsequent reaction(s) on other positions of the intermediate molecule and the protecting group can be selectively removed at the appropriate point without disrupting the remainder of the molecule including any other amino protecting group(s). Preferred amino protecting groups are t-butoxycarbonyl (t-Boc), allyloxycarbonyl, phthalimido, and benzyloxycarbonyl (CbZ).

※ Sugar moiety※ refers to a residue of a sugar compound having the following general structures:

wherein R, independently at each occurrence, is a hydrogen, azido, O—P, $NH_nP_{2-n}$ (n is 0 or 1), fluorine, $C_1$–$C_6$ alkyl, or another sugar moiety; and P is H, alkyl (e.g., methyl, ethyl, propyl, butyl, etc.), alkenyl (e.g., vinyl, allyl, etc.), acyl (e.g., acetyl), or a protecting group.

The literature describes the synthesis of a spirocyclic C-glycoside compound where X is a hydroxy group via the synthetic scheme illustrated in scheme 1 below; however, the reported yield is only about 34%. (see Barrett, A., et al. *J. Organic Chemistry*, 61(3), 1082 (1996).) When Applicants repeated the procedure described in Barrett, yields ranging from 5 to 20% were observed. Clearly, yields this low are unacceptable when the material is to be used as an intermediate.

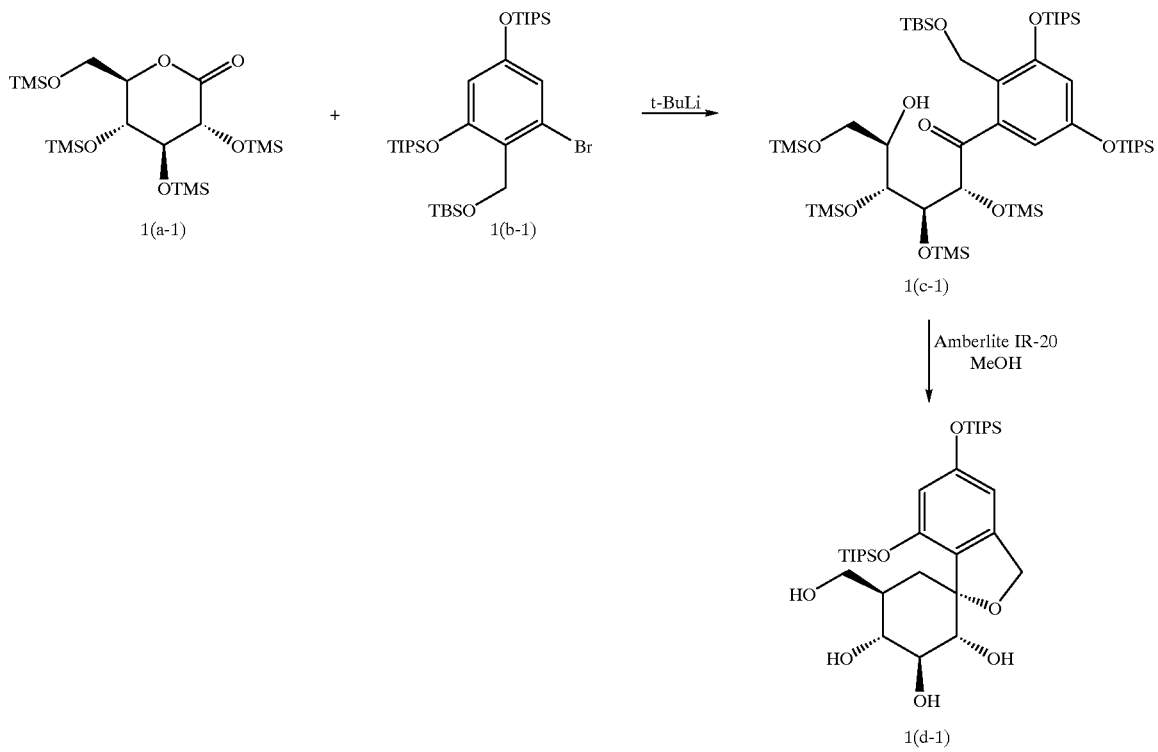

Scheme 1

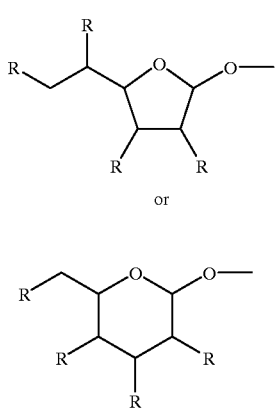

II

III

Several attempts were made to improve the yield of the spirocyclic C-glycoside using the procedures described in Barrett. Applicants have discovered several conditions having a significant impact on the final yield. For example, the temperature at which the lithium anion of 1(b-1) is added to the gluconolactone 1(a-1) plays an important role, as well as, the solvent within which the reaction is ran. When the lithium anion of 1(b-1) is formed and added at –78° C. to a solution of gluconolactone 1(a-1) at room temperature, a mixture of products was observed which indicates that both reagents must be mixed at –78° C. However, the reaction does not occur at –78° C. (see Example 1 below). Once the reagents are mixed at –78° C., the mixture is then allowed to quickly increase in temperature to initiate the reaction. The reaction mixture is preferably allowed to warm to room temperature within about 1 hour time period. Longer reaction times resulted in lower yields of the spiroketal 1(d-1) (20% to 40%). After the reaction is complete, the reaction product can be isolated using standard isolation procedures well-known to those skilled in the art. For example, the solvent is typically removed and then the residue purified via preparative chromatography.

Applicants also observed that reaction solvents, such as toluene and tetrahydrofuran (THF) resulted in little or no product. The preferred solvent is diethyl ether. The equivalents of bromide (e.g., bromide 1(b-1)) added also influenced the final yield. For example, equimolar amounts of the bromide and gluconolactone (e.g. gluconolactone 1(a-1)) gave poorer yields (30–40%) of the spiroketal compound (e.g., spiroketal 1(d-1)) than when an excess of the bromide is used. Preferably, greater than 1.0 equivalents of the bromide is added to the gluconolactone. Even though the addition of 2.0 equivalents did not appear to effect the yield, preferably the bromide is added at a level of about 1.5 equivalents to reduce costs. See Example 1 below for a more detailed description of the improved procedure which provided the spiroketal (spirocyclic C-glycoside compound) in a 60% yield.

The improved procedure for the preparation of a spirocyclic C-glycoside compound having the general structure I

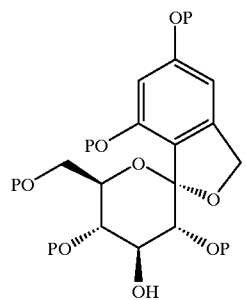

includes (i) mixing an alkyl lithium (e.g., methyl lithium, n-butyl lithium, t-butyl lithium, etc.) to a solution of Compound 1(b)

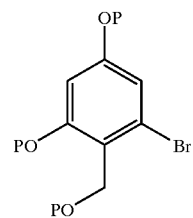

1(b)

where P is a protecting group, in diethyl ether at −78° C. to form a lithium anion solution; (ii) mixing the lithium anion solution at −78° C. with a solution of Compound 1(a)

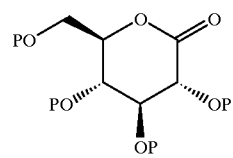

1(a)

where P is a protecting group, in diethyl ether cooled to −78° C.; (iii) allowing the mixture of step (ii) to warm quickly (approximately one hour) to room temperature; and (iv) isolating the desired spirocyclic C-glycoside compound.

Scheme 2 illustrates a new synthetic route for the production of a spirocyclic C-glycoside compound where X is a hydroxy group. The pentaacetylhexanoic acid salt starting material may be synthesized using the procedures described in Braun, C. E., et al., *Organic Synthesis*, 41, 79 (1961).

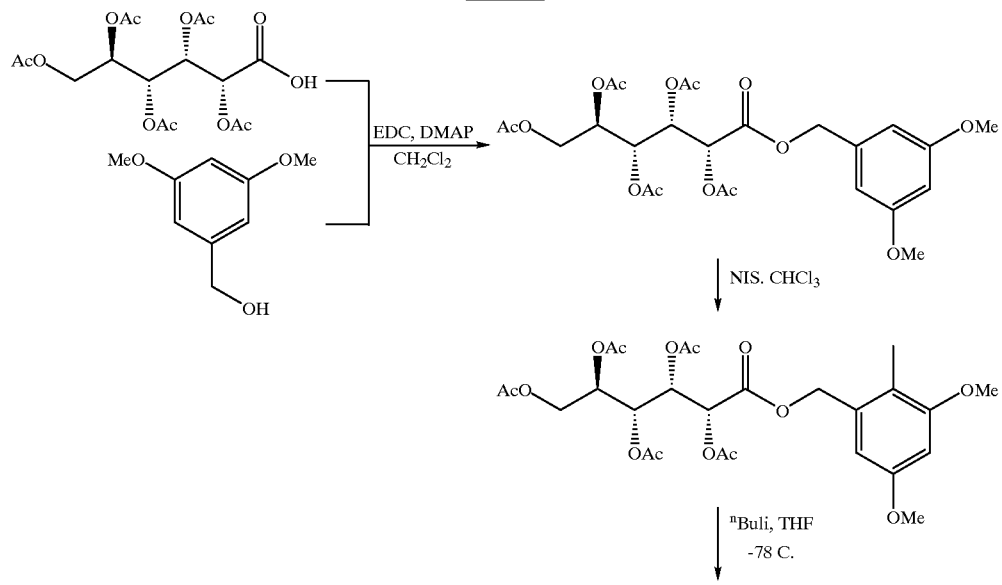

Scheme 2

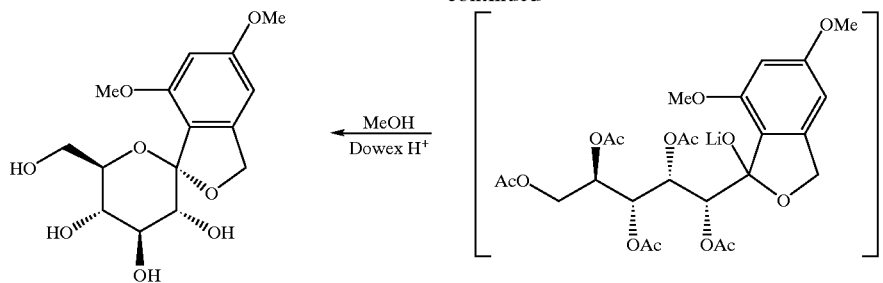

Scheme 3 illustrates an alternative route for the synthesis of a spirocyclic C-glycoside compound where X is a hydroxy group. In scheme 3, the iodo substituent is introduced into the synthetic scheme at an earlier stage of the synthesis. The iodine is added to the phenyl ring prior to the condensation with the acetylated hexanoic acid. Whereas, in scheme 2, the iodine was introduced onto the phenyl ring after condensation with the acetylated hexanonic acid.

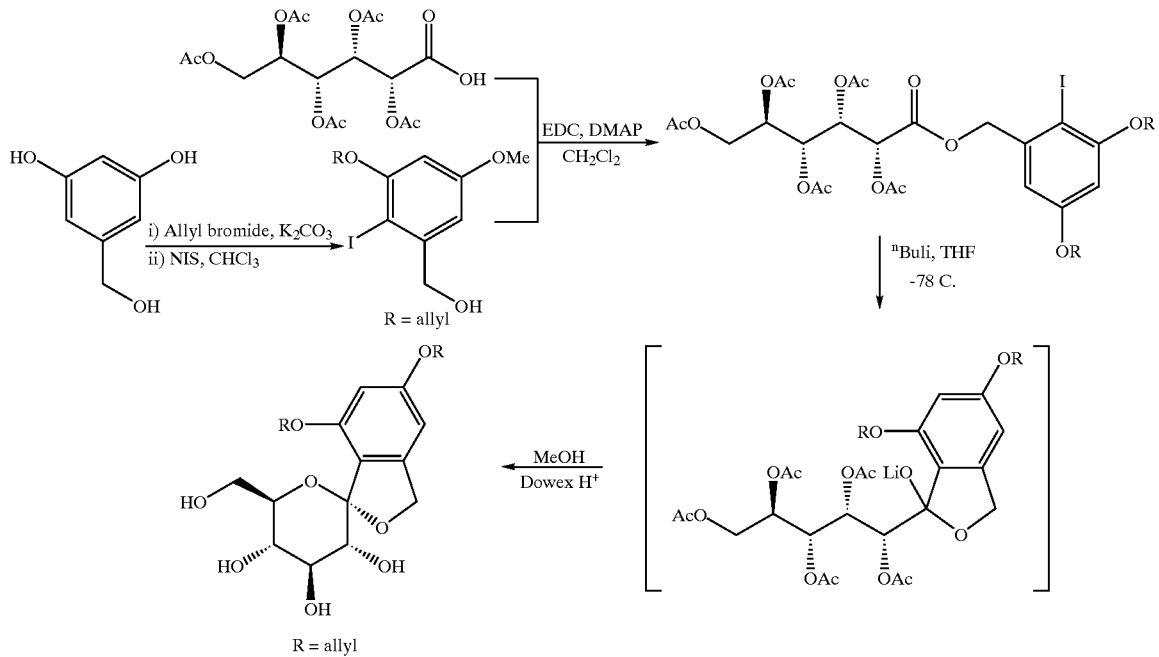

Scheme 4 illustrates the synthesis of a spirocyclic C-glycoside compound where X is an azide or amino group.

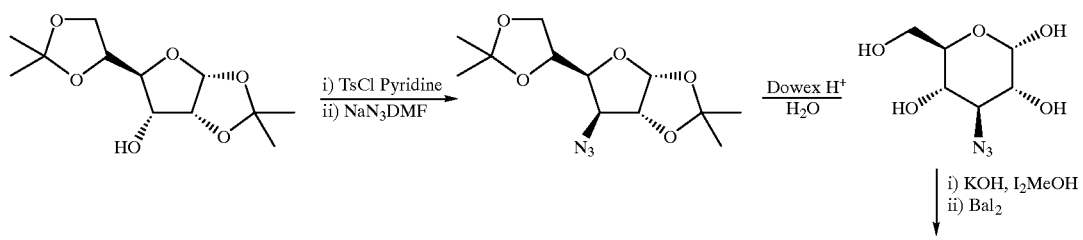

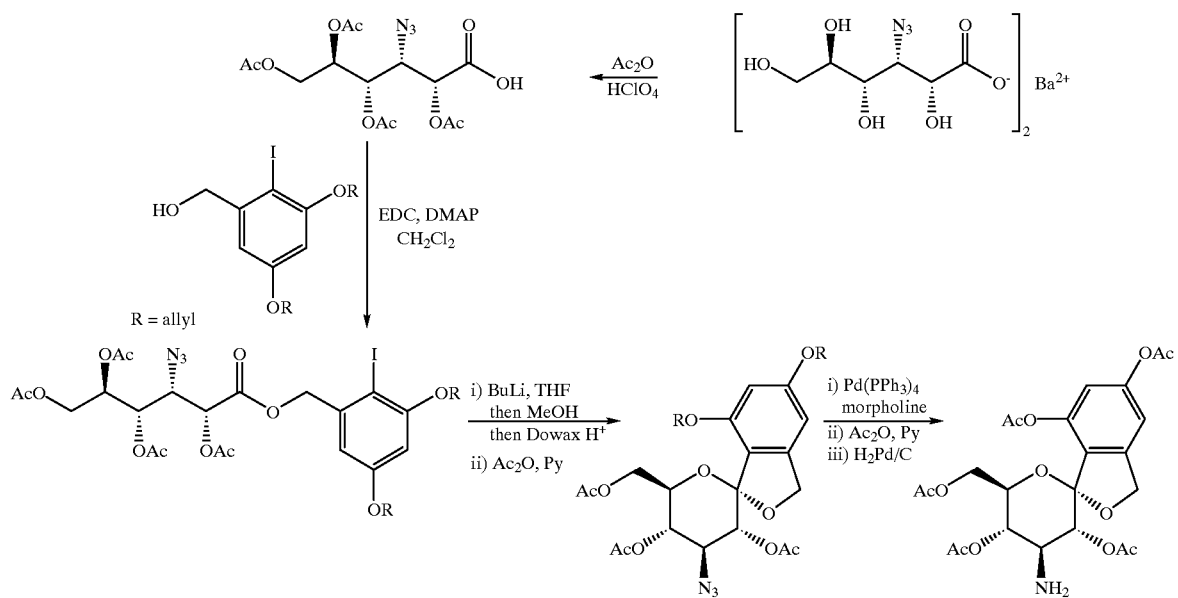
Scheme 5 illustrates the synthesis of a disaccharide spirocyclic C-glycoside compound.
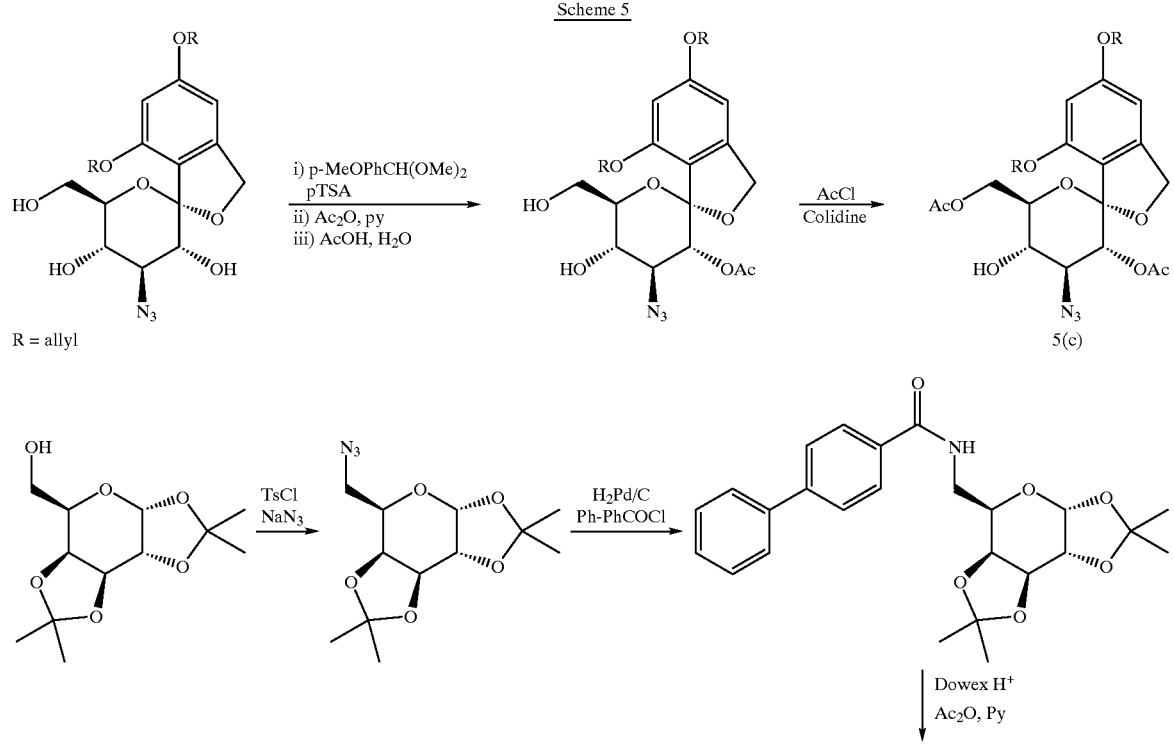

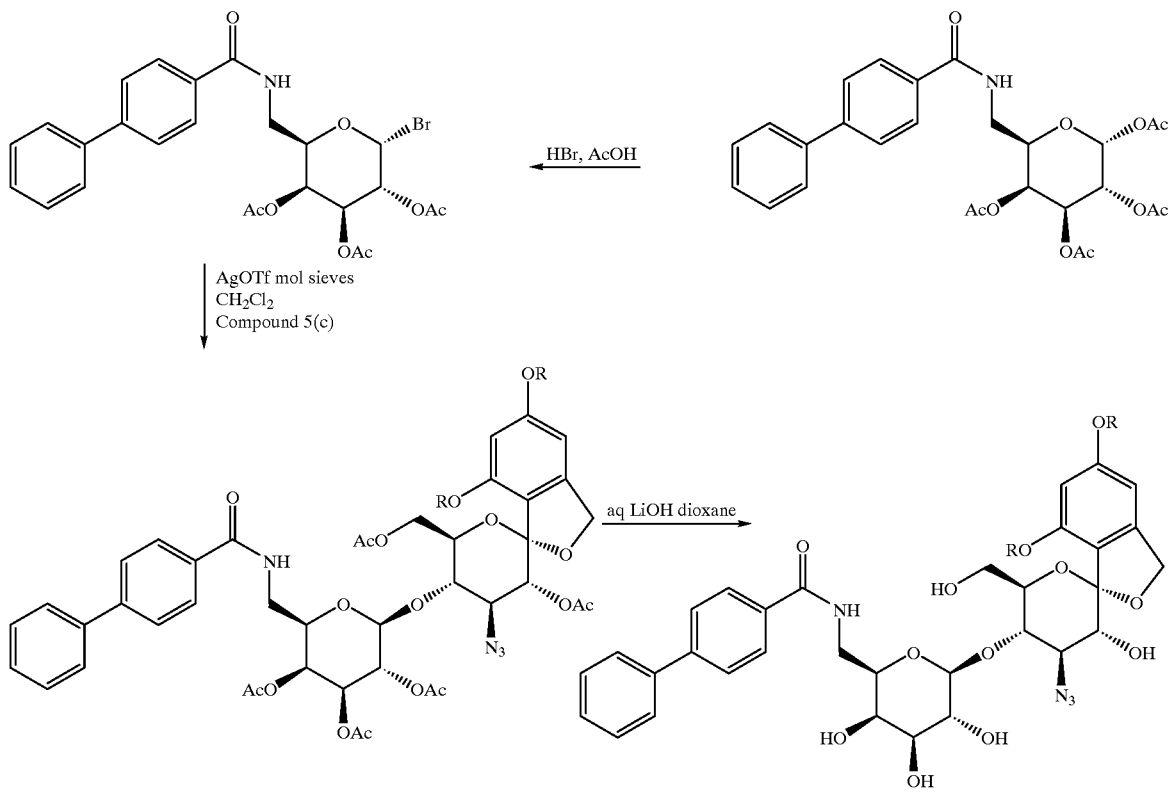

Those skilled in the art will appreciate that schemes 1, 2, 3, 4 and 5, and the examples below serve to illustrate the inventive processes and that other spirocyclic C-glycoside compounds represented by structure I may be synthesized using similar procedures.

EXAMPLES

Unless indicated otherwise, all chemicals can be acquired from commercial sources (i.e., Aldrich Chemical, Sigma, etc.) in reagent grade or better.

The acronyms used herein have the corresponding meanings:

TIPS refers to triisopropylsilyl
TMS refers to trimethylsilyl
TBDMS refers to t-butyl-dimethylsilyl
DMF refers to dimethylformamide
NBS refers to N-bromosuccinimide
NIS refers to N-iodosuccinimide
DMAP refers to dimethylaminopyridine
EDC refers to 1-(3-dimethylaminopropyl)-3-ethyl-carbodiimide hydrochloride

General Preparations

The pentaacetylhexanoic acid used in the following examples and illustrated below is prepared using the procedures described in Braun, C. E., *Organic Synthesis*, 41, 79 (1961).

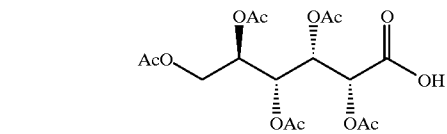

2,3,4,6-Tetra-O-(trimethylsilyl)-D-glucono-1,5-lactone 1(a) may be prepared as described in Horton, D. and W. Priebe, *Carbohydrate Res.*, 94, 27 (1981).

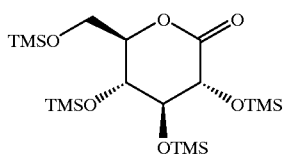

To a clear solution of D-gluconolactone (100 g, 561 mmol) in 940 ml of dry pyridine is added sequentiaLly hexamethyldisilazane (474 mL, 2247 mmol) and TMSCl (freshly distilled, 143 mL, 1127 mmol) under $N_2$. A white solid appeared immediately. After 60 minutes pyridine is removed to give a white solid. The solid is suspended in $CH_2Cl_2$ (1L) and filtered through celite. The cake is washed with more $CH_2Cl_2$ (500 ml). The solvent is evaporated, and the resulting orange oil is distilled in high vacuum (110–113° C./0.08 mm Hg), to give 256 g (97.7%) of the desired product as a pale yellow oil.

The bromide 1(b) may be prepared as described in Barrett, A., *J. Org. Chem.*, 61(3), 1082–1100 (1996) starting with 3,5-dihydroxybenzoate.

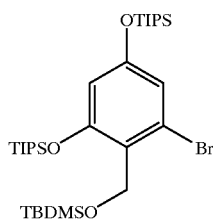

Methyl 3,5-Bis[(triisopropylsilyl)oxy]benzoate:

A colorless solution of methyl 3,5-dihydroxybenzoate (41.4 g, 250.4 mmol), TIPSCl (99.5 g, 516.05 mmol), Imidazole (45.8 g, 672.7 mmol) and DMAP (1.04 g) in dry DMF (200 ml) were stirred at room temperature for 24 hours. Water (400 ml) and ethyl acetate (400 ml) were added, and the mixture was stirred for an additional 30 minutes. The mixture was transferred to a decanting funnel, and the organic layer was washed with water (3×120 ml) and dried over $MgSO_4$. Filtration and concentration gave 118.1 g (quantitative) of an oil that was used in the next step without purification.

A sample was purified by chromatography to give the desired product (93%) (Rf 0.5 in hexane/ethyl acetate 95/5) as a colorless oil and a little amount (3%) of the monoprotected compound (Rf 0.19 in hexane/ethyl acetate 95/5) as a colorless oil.

3,5-Bis[(triisopropylsilyl)oxy]benzyl Alcohol:

In a two liter round bottom-flask equipped with a condenser and a addition funnel a solution of crude (118.1 g) in ethyl ether (800 ml) was added dropwise to a suspension of fine powered $LiAlH_4$ (9.32 g, 245.6 mmol) in ethyl ether (800 ml) at 0° C. under $N_2$ (exothermic reaction). Initially mixture turned yellow and the color disappears to give a white suspension. After the addition was complete, the reaction mixture was stirred then at room temperature for 2 hours. The suspension was cooled to 0° C. in an ice bath, then water (200 ml) was added very slowly through the funnel. A solution of KOH 1M (100 ml) was added and the mixture was stirred for 20 minutes. The resulting slurry mixture was filtered through celite. The cake was washed with more ethyl ether (150 ml). Filtration was very slow. The layers were separated, and the colorless organic layer was dried over $MgSO_4$. Filtration and concentration gave a colorless oil. Benzene (50 ml) was added and evaporated again to give 105.8 g (95%) of the alcohol as a colorless oil (Rf 0.15 in hexane/ethyl acetate 95/5) that was used in the next step without purification.

2-Bromo-3,5-Bis[(triisopropylsilyl)oxy]benzyl Alcohol:

NBS (43.66 g, 245.3 mmol) was added in 4 portions (at 15 minute intervals) to a solution of the alcohol (105.8 g, 233.6 mmol) in dry $CCl_4$ (790 ml). After the addition was completed, the mixture was stirred for 4 hours and then quenched with water (150 ml) and stirred for other 10 minutes. Organic layer was decanted, dried over $MgSO_4$. Filtration and evaporation gave 124 g (99%) of a pale yellow oil (Rf 0.4 in hexane/ethyl acetate 90/10).

tert-Butyl{[2-Bromo-3,5-Bis[(triisopropylsilyl)oxy]benzyl]oxy}dimethylsilane 1(b):

The crude bromoalcohol (124.3 g, 233.2 mmol), imidazole (47.7 g, 699.7 mmol), TBDMSCl (42.2 g, 279.7 mmol) and DMAP (515 mg) in dry $CH_2Cl_2$ (1300 ml) were stirred at room temperature for 24 hours. The solvent was removed and $EtOAc/H_2O$ (750 ml/750 ml) were added. After vigorous shaking for 10 minutes, the separated organic layer was washed with saturated aqueous NaCl (2×150 ml), dried over $MgSO_4$ and evaporated. The mixture was purified by column chromatography (hexane/ethyl acetate 98/2) to give 137.8 g (92%) of the TBDMS alcohol as a pale yellow oil (Rf 0.26 in hexane).

The following example is taken from Barrett, et al., *J. Org. Chem.*, 61(3), 1082–1100 (1996) for comparison to the improved synthesis described in Example 1.

COMPARATIVE EXAMPLE tert-Butyllithium (1.7 M in pentane, 15.65 mL, 2.2 equiv) was added to bromide 1(b) (8 g, 12.1 mmol) in $Et_2O$ (85 ml) at −78° C. and the mixture was stirred for 0.5 hour before being added, via cannula, to lactone 1(a) (5.66 g, 12.1 mmol) in $Et_2O$ (85 ml) at −78° C. The cannula was maintained at −78° C. with a dry ice pack. The mixture was stirred for 12 hours at −78° C. and then warmed up to room temperature, quenched with water (100 ml) and extracted with EtOAc. The organic phase was washed with brine, dried, filtered, and concentrated. The resultant yellow oil was dissolved in MeOH (150 ml), and Amberlite IR 120 (75 g) was added. After stirring for 16 hours, the Amberlite was removed by filtration and the MeOH evaporated. The oil was dissolved in EtOAc and extracted with water (2×) and brine. The organic layer was dried and purified by gradient chromatography (5–10% MeOH in $CHCl_3$) to give the title tetraol 1(d) (3.04 g, 34%) as an oil.

Example 1

Example 1 illustrates an improved procedure for the synthesis of spirocyclic C-glycoside compounds.

Preparation of Compound 1(d):

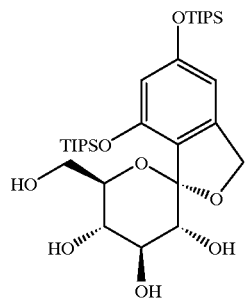

1(d)

The bromide 1(b) (11.6 g, 18.0 mmol, 1.5 equiv.) is dissolved in 30 ml of ethyl ether under $N_2$ and the solution is transferred to an addition funnel equipped with an external $CO_2$-acetone bath. To the cooled solution is added dropwise a 1.7M t-BuLi solution (22.2 ml, 37.8 mmnol). After 35 min at −78° C., the cold anion solution is added in one portion (10–20 seconds) to a solution of the gluconolactone 1(a) (6 g, 12.0 mmol in 40 ml of ethyl ether cooled to −78° C. After 1.5 hours at −78° C., the $CO_2$-acetone bath is removed and the reaction mixture is allowed to warm-up quickly to room temperature over 1 hour. The reaction is then quenched with water, extracted with EtOAc, washed with brine, dried over $MgSO_4$ and evaporated to dryness. The crude is dissolved in 160 ml of MeOH and treated with prewashed (MeOH) amberlite (80 g) for 16 hours. The reaction mixture is filtered and the solvent evaporated. The residue is purified by column chromatography (EtOAc, Rf 0.4) affording 4.7 g (60% yield) of pure product 1(d) as a white solid.

When an aliquot was transferred directly to water after 1.5 hours at −78° C. Extraction with EtOAc, drying and evaporation gave an oil which was a mixture of starting materials and no trace of intermediate ketone was detected. This confirms that the reaction does not take place at −78° C.

Example 2

Example 2 illustrates the preparation of a spirocyclic C-glycoside represented by structure I above where P is an allyl group using a new synthetic route.

Preparation of Compound 2(a):

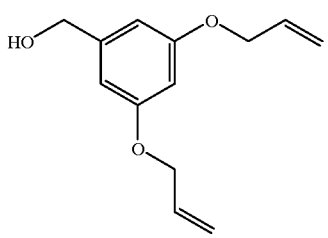

2(a)

Allyl bromide (11.48 g, 95 mmol) is added in one portion to a stirred mixture of potassium carbonate (26.22 g, 190 mmol) and 3,5-dihydroxybenzyl alcohol (6.64 g, 47.4 mmol) in acetone. The mixture is allowed to stir for 48 hours followed by removal of the solvent in vacuo. The residue is partitioned between water (100 ml) and diethyl ether (150 ml). The organic layer is separated, washed with water, brine, and then dried over magnesium sulfate ($MgSO_4$). Concentration in vacuo, afforded 10.5 g of a yellow oil which was purified by column chromatography on silica eluting with 10% ethyl acetate (EtOAc) in hexane, followed by 20%, 25% and finally 30% EtOAc to give 5.5 g of a colorless oil having a $^1$H-NMR that is consistent with structure 2(a).

Preparation of Compound 2(b):

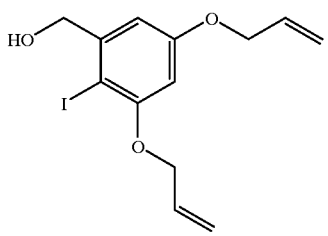

2(b)

N-iodosuccinimide (5.16 g, 23 mmol) is added in one portion to a solution of Compound 2(a) (2.5 g, 11.8 mmol) in 50 ml of chloroform ($CHCl_3$). The mixture is allowed to stir in the dark for 48 hours at room temperature. The solvent is then removed in vacuo. The residue is partitioned between diethyl ether and water. The organic layer is washed with 1N sodium thiosulfate, water and brine, and then dried over $MgSO_4$. The dried organic layer is concentrated in vacuo to afford 3.9 g (100% yield) of a pink solid having a $^1$H-NMR that is consistent with the structure 2(b).

Preparation of Compound 2(c):

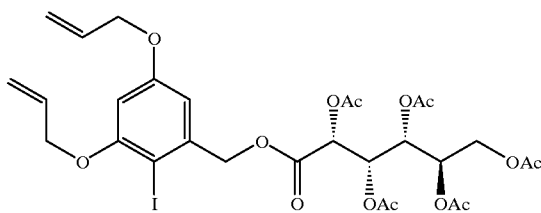

2(c)

EDC (2.3 g, 12 mmol) is added in one portion to a stirred solution of pentaacetylhexanonic acid (4.9 g, 12 mmol), Compound 2(b) (3.8 g) and 10 mg of N,N-dimethylaminopyridine (DMAP) in 40 ml of dry methylene chloride ($CH_2Cl_2$). The mixture is allowed to stir for 16 hours under a nitrogen atmosphere. The solvent is removed in vacuo and the residue partitioned between diethyl ether and water. The organic layer is washed with saturated sodium bicarbonate, 1N hydrochloric acid, water and then brine. The solution is concentrated in vacuo after drying over $MgSO_4$. The residue is purified by column chromatography on silica eluting with a gradient of ethylacetate (30%, 40%, 50%) in hexane to afford 6.7 g (83% yield) of a compound having a $^1$H-NMR that is consistent with Compound 2(c).

Preparation of Compound 2(d):

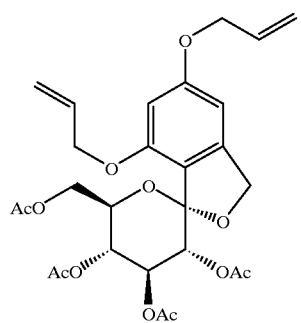

2(d)

Compound 2(c) is dried prior to use by dissolving in 100 ml of benzene, concentrating in vacuo, releasing the vacuum to argon and then dried further under high vacuum overnight. A solution of n-butyl lithium (1.6 M) in hexane (6.8 ml, 10.9 mmol) is added dropwise to a stirred solution of Compound 2(c) (4.0 g, 5.46 mmol) in 125 ml of dry tetrahydrofuran (THF) at −78° C. under argon whereupon a yellow color forms. The mixture is stirred for 30 minutes at −78° C. before addition of 200 ml of methanol and subsequent removal of the cooling bath. The mixture is stirred for 16 hours at room temperature and then 30 g of Dowex 50x8-100 ion exchange resin (previously washed with methanol) is added. The mixture is stirred for an additional 16 hours then filtered and concentrated in vacuo. The residue is dissolved in 100 ml of pyridine followed by the addition of acetic anhydride (60 ml). After 16 hours, the mixture is concentrated in vacuo and the residue partitioned between ethylacetate and 1 N HCl. The organic layer is washed with saturated aqueous sodium bicarbonate, water and brine, and then dried over $MgSO_4$ before concentrating in vacuo. The residue is purified by column chromatography on silica eluting with 40% ethylacetate in hexane to give 1.95 g (66% yield) of a colorless oil having a $^1$H-NMR that is consistent with structure 2(d).

Example 3

Example 3 further illustrates the preparation of spirocyclic C-glycoside compounds represented by structure I described earlier.

Preparation of Compound 3(a):

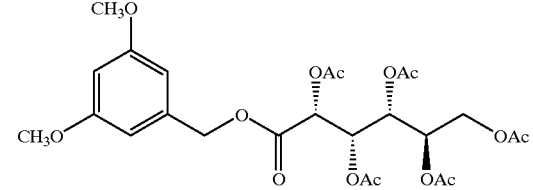

3(a)

The same general procedure described for the preparation of Compound 2(c) in Example 2 is used to prepare Compound 3(a) using the following materials in the corresponding amounts:

| pentaacetylhexanonic acid: | 16.6 g, 40.9 mmol |
|---|---|
| 3,5-dimethoxybenzyl alcohol: | 4.6 g, 45.0 mmol |
| EDCI: | 9.4 g, 45.0 mmol |
| N,N-dimethylaminopyridine: | 150 ml |
| Methylene chloride: | 100 ml |

The crude material, after aqueous work-up and concentration in vacuo, is triturated twice with 20% ethylacetate in hexane. The residue is then puruifed by column chromatography on silica eluting with 100% methylene chloride, 18% ethylacetate in methylene chloride, and 20% ethylacetate in methylene chloride to afford 16.6 g (75% yield) of a colorless oil (which solidified upon standing) having a $^1$H-NMR that is consistent with structure 3(a)

Preparation of Compound 3(b):

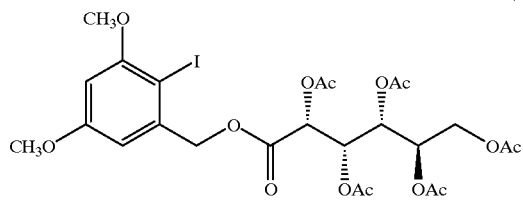

3(b)

A solution of Compound 3(a)(1.51 g, 2.7 mmol) and N-iodosuccinimide (672 mg, 3.0 mmol) in chloroform is heated to 50° C. for 24 hours. The cooled purple mixture is washed with water, 1N sodium thiosulfate, saturated aqueous sodium bicarbonate and brine. The organic layer is dried over MgSO4 and then concentrated in vacuo to afford 1.8 g of a white solid having a $^1$H-NMR consistent with structure 3(b) The material also contained about 15% of unreacted starting material. The mixture was used in the next step of the synthesis without further purification.

Preparation of Compound 3(c):

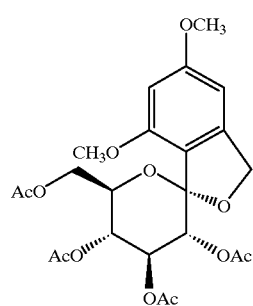

2(c)

Compound 3(c) is prepared using the same procedure as described for the preparation of 2(d) in Example 2. The $^1$H-NMR of the isolated compound is consistent with structure 3(c).

Example 4

Example 4 illustrates the synthesis of novel amino analogs of spirocyclic C-glycoside compounds represented by structure I described earlier.

Preparation of Compound 4(a):

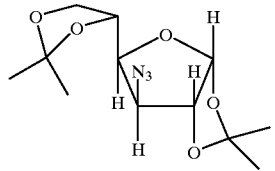

4(a)

Tosyl chloride (3.90 g, 20.5 mmol) is added to a solution of 1,2,5,6-diacetone-D-allofuranone (5.07 g, 19.5 mmol) in 20 ml of pyridine. The mixture is stirred for 16 hours at room temperature. The residue is poured into ice-water whereupon a precipitate is formed. The precipitate is filtered and dried overnight in a vacuum desicator over phorphorus pentoxide. $^1$H-NMR confirms the formation of the corresponding tosylate. The solid is then dissolved in 100 ml of dimethylformamide (DMF) and sodium azide (12.8 g) is added. The mixture is heated to reflux for 48 hours whereupon the mixture turned black. The mixture is then cooled and concentrated in vacuo. The residue is partitioned between water and ethylacetate. The organic layer is washed twice with water followed by a brine solution and then dried over MgSO$_4$. The concentrate is purified by column chromatography on silica eluting with 10% ethylacetate in hexane to afford 2.63 (45% yield) of a colorless oil having a $^1$H-NMR that is consistent with structure 4(a).

Preparation of Compound 4(b):

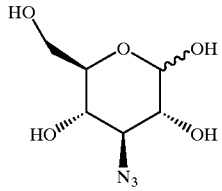

4(b)

Compound 4(a) (400 mg, 1.4 mmol) is heated to 60° C. for 16 hours in 2 ml of water containing 600 mg of Dowex 50x8-100 resin. The mixture is cooled, filtered and concentrated in vacuo to afford 260 mg (92% yield) of a white solid having a $^1$H-NMR that is consistent with structure 4(b).

Preparation of Compound 4(c):

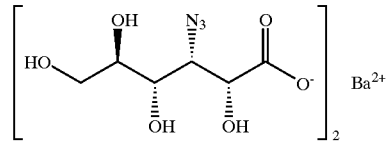

4(c)

A solution of iodine (2.85 g) in 20 ml of methanol is warmed to 40° C. followed by the addition of a solution of Compound 4(b) in 5 ml of methanol. The heat is removed and a solution of potassium hydroxide in 33 ml of methanol is added dropwise over 10 minutes. After 10 additional minutes, a solution of potassium hydroxide in 25 ml of methanol is added dropwise followed by stirring for 20 minutes. A solution of Barium iodide (2.5 g) in methanol is added dropwise followed by stirring for 10 minutes. The precipitate formed is centrifuged, re-suspended in methanol, centrifuged again and then dried under high vacuum for 24 hours to afford 1.4 g of a solid material (structure 4(c)).

Preparation of Compound 4(d):

A 70% aqueous perchloric acid (1.45 g) is added dropwise with stirring to 14 ml of acetic anhydride cooled in an ice-bath, while maintaining the rate of addition such that the temperature remained below 20° C. Compound 4(c) (1.4 g, 2.4 mmol) is added portionwise to the mixture while maintaining the temperature below 40° C. The mixture is then heated to 40° C. for 20 minutes then cooled, poured into 10 ml of ice-water and stirred for 1 hour. The mixture is extracted with $CHCl_3$ (3×50 ml) and the combined extracts washed with water, dried over magnesium sulfate and concentrated in vacuo to afford 1.8 g of a white solid (structure 4(d)).

Preparation of Compound 4(e):

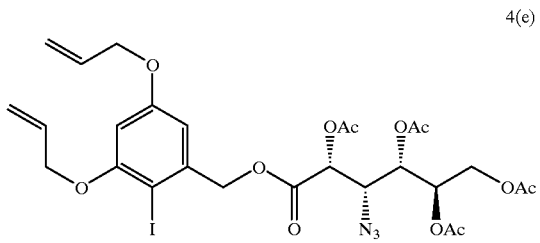

4(e)

Compound 4(e) is prepared using the same general procedure as described in Example 2 for the preparation of Compound 2(c) using the following materials in the corresponding amounts:

| | |
|---|---|
| Compound 2(b) from Example 1: | 5.0 g, 14.5 mmol |
| Compound 4(d): | 9.1 g, 23.4 mmol |
| EDC: | 4.2 g, 21.9 mmol |
| N,N-dimethylaminopyridine: | 88 mg, 0.72 mmol |
| Methylene Chloride: | 150 ml |

The crude material was purified using column chromatography on silica eluting with 25% to 30% ethylacetate in hexane to afford 8.1 g of a compound having a $^1$H-NMR that is consistent with structure 4(e) and 2.0 g of impure compound.

Preparation of Compound 4(f):

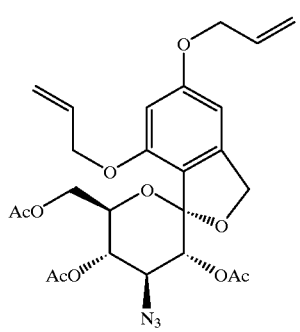

4(f)

Compound 4(e) is dried prior to use by dissolving in 100 ml of benzene, concentrating in vacuo, releasing the vacuum to argon and then dried further under high vacuum overnight. n-Butyl lithium (1.13 ml) in hexane (1.6 m, 1.82 mmol) is added dropwise over 10 min to a solution of Compound 4(e) (650 mg, 0.91 mmol) in 20 ml of anhydrous THF at −78° C. under argon, allowing the solution to run down the inside of the walls of the flask during the addition. After stirring at −78° C. for 20 minutes, 20 ml of methanol is added and the cold bath removed. The mixture is allowed to warm to ambient temperature and stirred for 16 hours. The pH of the mixture was then adjusted to 1–2 via addition of Dowex 50X8 100 (H+ form) ion exchange resin and the mixture stirred for an additional 3 hours. The mixture is filtered, concentrated in vacuo and 16 ml of pyridine and 8 ml of $Ac_2O$ is added. The mixture is stirred for 16 hours, concentrated in vacuo and the residue chromatographed on silica eluting with a gradient of 25% to 30% EtOAc in hexane to afford 220 mg (41% yield) of a colorless oil having a $^1$H-NMR that is consistent with structure 4(f).

Preparation of Compound 4(g):

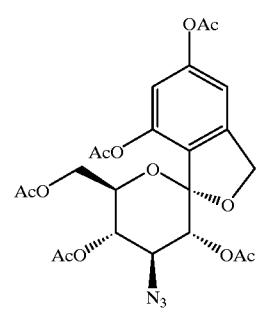

4(g)

A solution of Compound 4(f) (150 mg, 0.28 mmol) in 15 ml of anhydrous THF is purged with argon and 33 mg of $Pd(PPh_3)_4$ (0.03 mmol) is added under argon followed by the addition of 465 mg of morpholine (5.67 mmol). The mixture is stirred at ambient temperature under argon for 6 hours and then concentrated in vacuo. The residue is partitioned between EtOAc and 1N HCl and the organic layer separated, washed with 1N HCl, brine, dried over $MgSO_4$ and concentrated in vacuo. The residue is dissolved in 4 ml of pyridine and 2 ml of $Ac_2O$ is added followed by stirring at ambient temperature for 16 hours. The mixture is then concentrated in vacuo and the residue chromatographed on silica eluting with 40% EtOAc in hexane to afford 108 mg (72% yield) of a colorless oil having a $^1$H-NMR that is consistent with structure 4(g)

Preparation of Compound 4(h):

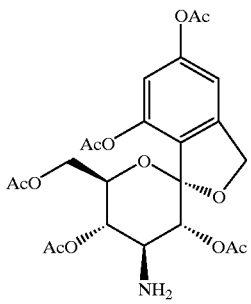

4(h)

A vigorously stirred mixture of Compound 4(g) (62 mg, 0.12 mmol) and 100 mg of 10% Pd/C in 10 ml of EtOH previously purged with $N_2$ is subjected to hydrogenation under 1 atm. of $H_2$ for 30 minutes. The mixture is again purged with $N_2$, filtered and concentrated in vacuo to afford 42 mg (72% yield) of a white powder having a $^1$H-NMR that is consistent with structure 4(h).

Example 5

Example 5 illustrates the preparation of a disaccharide spirocyclic C-glycoside compound.

Preparation of Compound 5(a):

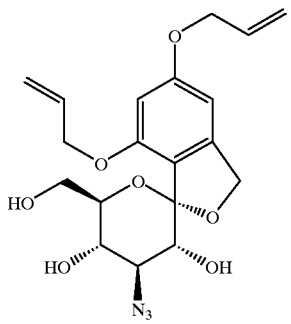

5(a)

Compound 4(e) is dried prior to use by dissolving in 100 ml of benzene, concentrating in vacuo, releasing the vacuum to argon and then dried further under high vacuum overnight. n-Butyl lithium (7.9 ml) in hexane (1.6 m, 12.6 mmol) is added dropwise over 10 minutes to a solution of 4.5 g (6.3 mmol of Compound 4(e) from Example 4 in 150 ml of anhydrous THF at −78° C. under argon, allowing the solution to run down the inside of the walls of the flask during the addition. After stirring at −78° C. for 20 minutes, 150 ml of methanol is added and the cold bath removed. The mixture is allowed to warm to ambient temperature and stirred for 16 hours. The pH of the mixture is then adjusted to 1–2 via addition of Dowex 50X8 100 (H+ form) ion exchange resin and the mixture is stirred for an additional 3 hours. The mixture is filtered, concentrated in vacuo and the residue chromatographed on silica eluting with a solvent gradient of 3% to 5% methanol in $CHCl_3$ to afford 1.05 g (42% yield) of a pale yellow solid having a $^1$H-NMR that is consistent with structure 5(a).

Preparation of Compound 5(b):

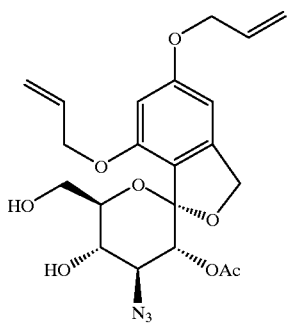

5(b)

p-Toluenesulfonic acid (230 mg, 1.2 mmol) is added in one portion to a solution of Compound 5(a)(4.90 g, 12.1 mmol) and anisaldehyde dimethyl acetal (2.86 g, 15.7 mmol) in 80 ml anhydrous DMF. The mixture is stirred under vacuum for 0.5 hour and then 10 ml of triethylamine is added. The solvent is removed in vacuo and the residue is dissolved in 60 ml of pyridine. $Ac_2O$ (30 ml) is added and the mixture stirred at ambient temperature for 16 hours. The mixture is then concentrated in vacuo to afford 6.51 g of crude product. A portion (3 g) of the crude material is dissolved in 24 ml of AcOH and 6 ml of water and stirred at ambient temperature for 2 hours. The mixture is then concentrated in vacuo and the residue purified by chromatography on silica eluting with 3:2; EtOAc:hexane to afford 1.13 g (45% yield) of white solid having a $^1$H-NMR that is consistent with structure 5(b).

Preparation of Compound 5(c):

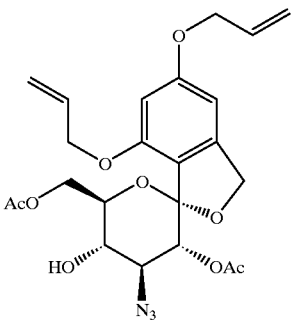

5(c)

2,4,6-Collidine (54 mg, 0.44 mmol) is added to a stirred solution of Compound 5(b)(101 mg, 0.22 mmol) in 2 ml of anhydrous $CH_2Cl_2$ at −78° C. under argon followed by AcCl (18 mg, 0.22 mmol). The mixture is allowed to warm to ambient temperature over 6 hours and stirred for a further 10 hours. The mixture is then washed with 1 N HCl, water, dried over magnesium sulfate and concentrated in vacuo. The residue is purified by chromatography on silica eluting with 1:1 EtOAc:hexane to afford 86 mg (78% yield) of a white solid having a $^1$H-NMR that is consistent with structure 5(c).

Preparation of Compound 5(d):

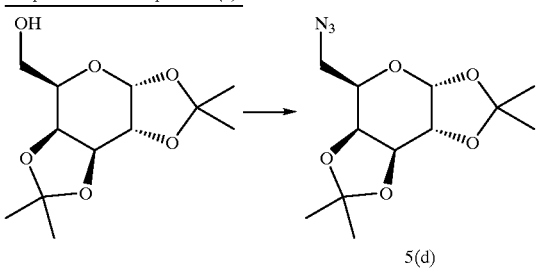

5(d)

Tosyl chloride (19.2 g, 0.10 mol) is added in one portion to a stirred solution of 25.0 g of 1,2,3,4-diisopropylidene-D-galactopyranose (96 mmol) in 100 ml of pyridine. The mixture is allowed to stir at ambient temperature for 48 hours. The mixture is then poured onto ice-water and extracted with EtOAc. The organic extract is washed with 1N HCl, sat. aq. sodium bicarbonate and water, dried over magnesium sulfate and concentrated in vacuo. The crude product (41.0 g) is dissolved in 150 ml of DMF, sodium azide (25 g, 0.39 mol) is added and the mixture is heated to 140° C. for 16 hours. Additional sodium azide (25 g, 0.39 mol) is added and the mixture heated to 140° C. for a further 72 hours before cooling and filtering. The filtrate is concentrated in vacuo and the residue partitioned between EtOAc and water. The organic layer is dried over magnesium sulfate and concentrated in vacuo to afford 25.5 g of a brown oil which is used in the subsequent step without further purification.

Preparation of Compound 5(e):

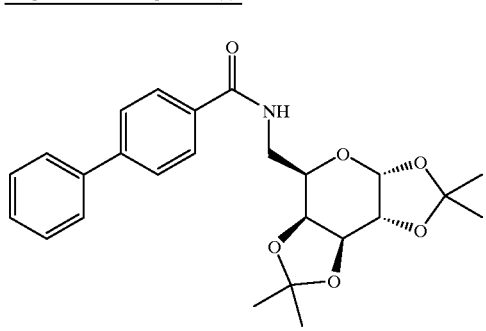

5(e)

A vigorously stirred mixture of Compound 5(d)(3.0 g, 10.5 mmol) and 1 g of 10% Pd/C in 150 ml of MeOH previously purged with $N_2$ is subjected to hydrogenation under 1 atm of $H_2$ for 16 hours. The mixture is again purged with $N_2$, filtered and concentrated in vacuo. The residue is dissolved in 25 ml of $CH_2Cl_2$ and 2.2 ml(16.6 mmol) of 2,4,6-collidine is added followed by portionwise addition of the acid chloride (2.2 g, 10.2 mmol). The mixture is stirred for 16 hours then poured into 1N HCl and the organic layer separated, washed with sat. aq. sodium bicarbonate, dried over magnesium sulfate and concentrated in vacuo to afford 4.1 g (94% yield) of the desired amide. The material is used in the next step without further purification.

Preparation of Compound 5(f):

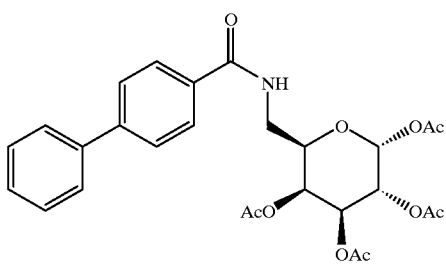

5(f)

Compound 5(e)(3.1 g, 5.8 mmol) is suspended in 80 ml of water and 15 g of Dowex 50X8 100 (H+ form) ion exchange resin is added. The mixture is heated to 80° C. for 16 hours after which time little reaction had occurred. THF (40 ml) is then added to dissolve the solid and the mixture is heated to 80° C. for 48 hours. The mixture is cooled, filtered and concentrated in vacuo. The residue is dissolved in 40 ml of pyridine and 20 ml of $Ac_2O$ is added. The mixture is stirred at ambient temperature for 16 hours. The mixture is then concentrated in vacuo and chromatographed on silica eluting with 1:1 EtOAc:hexane to affore 1.6 g (41% yield) of a colorless oil having a $^1$H-NMR that is consistent with structure 5(f).

Preparation of Compound 5(g):

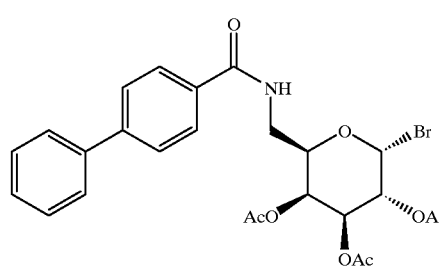

5(g)

33% HBr in acetic acid (4 ml) is added to a mixture of Compound 5(f)(1.50 g, 2.8 mmol) in 1.6 ml of AcOH and 0.8 ml of $Ac_2O$ at 0° C. over 5 min. After stirring at 0° C. for 0.5 hour, the mixture is allowed to warm to ambient temperature. After stirring for an additional 2 hours, 10 ml of $CH_2Cl_2$ is added and the organic layer separated washed with ice-cold water, ice-cold sat. aq. sodium bicarbonate (x 3), dried over magnesium sulfate and concentrated in vacuo to afford 1.48 g (95% yield) of a white powder having a 1H-NMR that is consistent with structure 5(g).

Preparation of Compound 5(h):

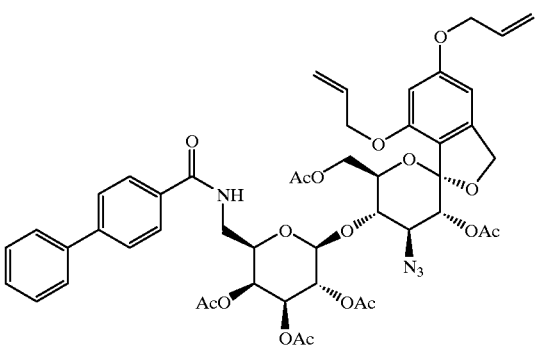

5(h)

A mixture of the alcohol 5(c) (550 mg, 0.11 mmol), and bromosugar 5(g)(740 mg, 1.35 mmol) is dried by dissolving in 10 ml of benzene and concentrating in vacuo (repeated twice) while releasing the vacuum to argon on each occasion. Flame-dried, powdered 4A molecular sieves (2 g) are added followed by 10 ml of anhydrous $CH_2Cl_2$ and the mixture is allowed to stir under argon for 0.5 hour. Silver trifluoromethanesulfonate (403 mg, 1.57 mmol) is then added and the mixture stirred in the dark under argon for 16 hours. Acetone (10 ml) is added and the mixture filtered and washed with 1:1 $CH_2Cl_2$:acetone. The combined filtrate and washings are concentrated in vacuo and the residue purified by chromatography on silica eluting with a gradient of 30% to 35% EtOAc in toluene to afford 810 mg (76% yield) of a white solid having a $^1$H-NMR that is consistent with the disaccharide 5(h).

Preparation of Compound 5(i):

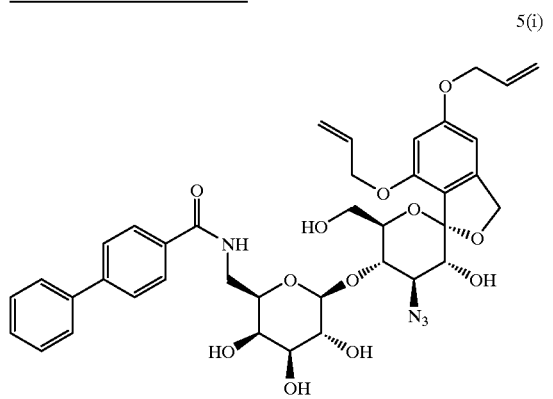

5(i)

LiOH.H$_2$O (150 mg, 3.6 mmol) is added to a solution of Compound 5(h) (400 mg, 0.42 mmol) in 4 ml of dioxane and 2 ml of water. The mixture is stirred at ambient temperature for 16 hours. The mixture is acidified to a pH of 4 by the addition of Dowex 50X8 100 (H+ form) ion exchange resin then filtered and concentrated in vacuo to afford 310 mg (99% yield) of a white solid having a $^1$H-NMR that is consistent with structure 5(i).

We claim:

1. A spirocyclic C-glycoside compound having structure I:

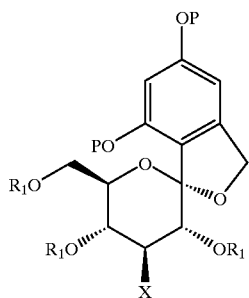

I wherein P is H, alkyl, alkenyl, acyl, or a protecting group; X is SR$_1$, N$_3$, or NH$_n$(R$_1$)$_{2-n}$, where n=0 or 1; and R$_1$ is the same as P or a sugar moiety represented by structure II or III:

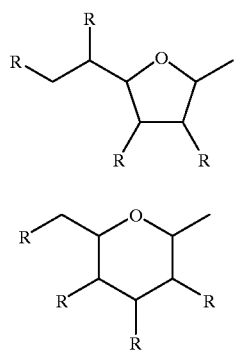

II

III wherein R, independently at each occurrence, is a hydrogen, fluorine, C$_1$–C$_6$ alkyl, azido, O—P, NH$_n$P$_{2-n}$, where n is 0 or 1, or another sugar moiety; and P is H, alkyl, alkenyl, acyl, or a protecting group.

2. A process for preparing a spirocyclic C-glycoside compound having structure IA

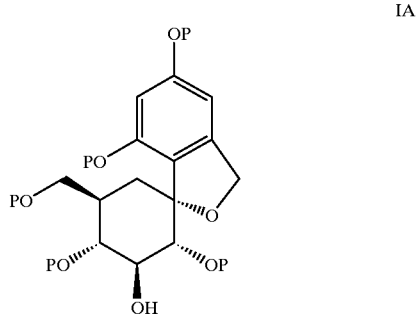

IA wherein P is a protecting group, comprising the steps of:

(i) mixing an alkyl lithium with a solution of Compound 1(b)

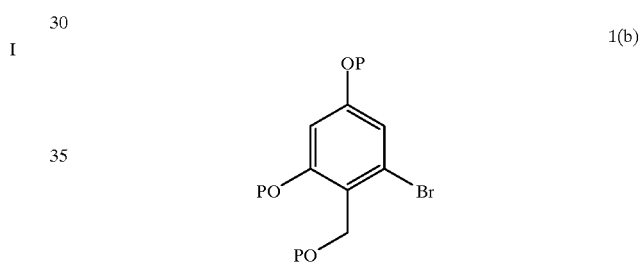

1(b)

where P is a protecting group, in diethyl ether at −78° C. to form a lithium anion solution;

(ii) mixing said lithium anion solution at −78° C. with a solution of Compound 1(a)

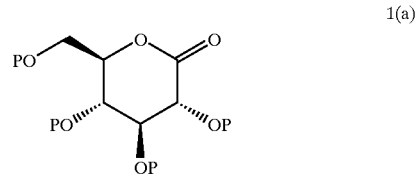

1(a)

where P is a protecting group, in diethyl ether cooled to −78° C.;

(iii) allowing said mixture of step (ii) to warm quickly to room temperature; and (iv) isolating said spirocyclic C-glycoside compound.

3. The process of claim 2 wherein said Compound 1(b) is present in an amount equal to at least 1.5 equivalents.

4. A process for preparing a spirocyclic C-glycoside compound represented by structure IB

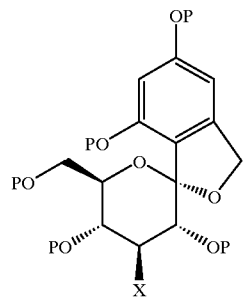

IB wherein X is OP, SP, or an azide group and P is each independently a hydrogen, alkyl, alkenyl, acyl, or a protecting group, comprising the steps of:

(i) condensing iodo Compound 1(a)

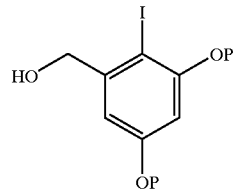

1(a)

where P has the same meaning as above, with Compound 1(b)

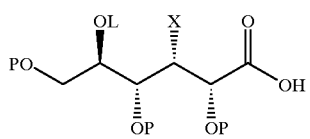

1(b)

where P has the same meaning as above and L is a leaving group, to form an ester 1(c)

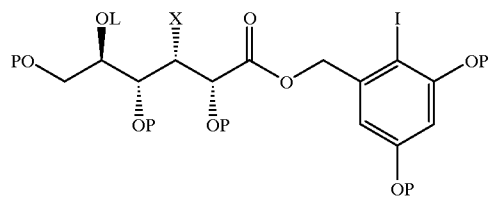

1(c)

where P and L have the same meaning as above;

(ii) treating said ester 1(c) with an alkyl lithium; and (iii) optionally replacing any P groups that may have been removed during step (ii) which may be the same or different to form said spirocyclic C-glycoside compound represented by structure I.

5. The process of claim 4 further comprising the step of reducing said azide group to an amino group when X is azide.

6. A process for preparing a spirocyclic C-glycoside compound represented by structure I

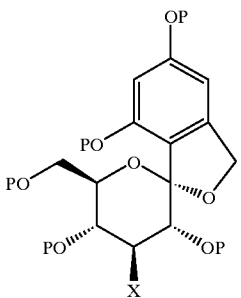

I wherein X is OP, SP, or an azide group and P is each independently a hydrogen, alkyl, alkenyl, acyl, or a protecting group, comprising the steps of:

(i) condensing Compound 1(a)

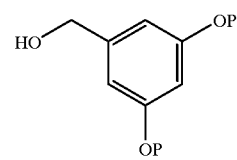

1(a)

where P has the same meaning as above, with Compound 1(b)

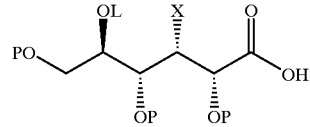

1(b)

where P has the same meaning as above and L is a leaving group, to form an ester 1(c)

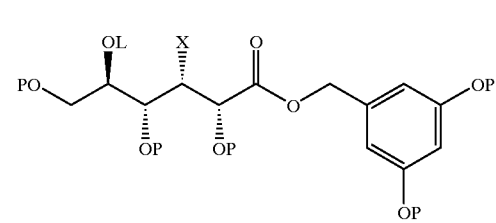

1(c)

where P and L have the same meaning as above;

(ii) treating Compound 1(c) with N-iodosuccinimide to form iodo Compound 1(d)

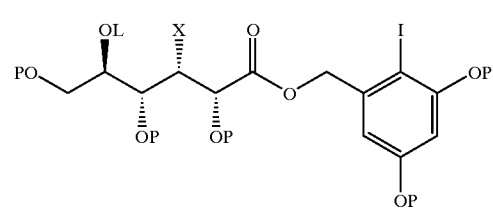

1(d)

where P and L have the same meaning as above;

(iii) treating said ester 1(d) with an alkyl lithium; and
(iv) optionally replacing any P groups that may have been removed during step (iii) which may be the same or different to form said spirocyclic C-glycoside compound represented by structure I.

7. The process of claim 6 further comprising the step of reducing said azide group to an amino group when X is azide.

* * * * *